United States Patent
Themelis

(10) Patent No.: US 11,042,014 B2
(45) Date of Patent: Jun. 22, 2021

(54) CATADIOPTRIC MEDICAL IMAGING SYSTEM FOR OBSERVING THE INSIDE WALL OF A SURGICAL CAVITY

(71) Applicant: LEICA INSTRUMENTS (SINGAPORE) PTE. LTD., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 132 days.

(21) Appl. No.: 16/293,747

(22) Filed: Mar. 6, 2019

(65) Prior Publication Data
US 2019/0278069 A1 Sep. 12, 2019

(30) Foreign Application Priority Data
Mar. 6, 2018 (EP) .................................... 18160210

(51) Int. Cl.
| | | |
|---|---|---|
| G02B 17/08 | (2006.01) | |
| A61B 90/00 | (2016.01) | |
| G02B 21/00 | (2006.01) | |
| G02B 13/06 | (2006.01) | |
| A61B 5/00 | (2006.01) | |

(Continued)

(52) U.S. Cl.
CPC ........ *G02B 17/0856* (2013.01); *A61B 90/361* (2016.02); *G02B 13/06* (2013.01); *G02B 17/08* (2013.01); *G02B 17/0804* (2013.01); *G02B 17/0892* (2013.01); *G02B 21/0012* (2013.01); *A61B 5/0075* (2013.01); *A61B 90/20* (2016.02); *A61B 2090/309* (2016.02); *A61B 2090/3618* (2016.02); *A61B 2090/371* (2016.02); *A61B 2090/372* (2016.02); *A61B 2090/3941* (2016.02); *G02B 17/023* (2013.01);
(Continued)

(58) Field of Classification Search
CPC . A61B 90/361; A61B 2090/371; A61B 90/20; A61B 2090/3618; A61B 2090/309; A61B 2090/3941; A61B 2090/372; A61B 5/0075; A61B 90/30; G02B 17/0856; G02B 13/06; G02B 17/08; G02B 17/0804; G02B 17/0892; G02B 21/0012; G02B 21/025; G02B 21/04; G02B 17/023; G02B 21/02
See application file for complete search history.

(56) References Cited

U.S. PATENT DOCUMENTS

| | | |
|---|---|---|
| 2004/0033426 A1 | 2/2004 | Den Boef et al. |
| 2005/0049462 A1 | 3/2005 | Kanazawa |

(Continued)

FOREIGN PATENT DOCUMENTS

| | | |
|---|---|---|
| DE | 102008041910 A1 | 11/2009 |
| JP | H07163517 A | 6/1995 |

(Continued)

*Primary Examiner* — Tuyen Tra
(74) *Attorney, Agent, or Firm* — Hodgson Russ LLP

(57) ABSTRACT

The invention relates to a catadioptric medical imaging system (1), in particular a surgical microscope (2). During surgery, it may be necessary to gain more information about a surgical cavity (6), in particular the type of tissue (29) at the inside walls (4) of the surgical cavity (6). To solve this problem, the catadioptric medical imaging system (1) according to the invention comprises a camera device (8) and a convex catoptric mirror (20) adapted to be inserted into the surgical cavity (6). The catoptric mirror (20) is mounted on an arm (22) and spaced apart from the camera device (8).

13 Claims, 1 Drawing Sheet

(51) Int. Cl.
   *G02B 17/02*    (2006.01)
   *G02B 21/02*    (2006.01)
   *A61B 90/20*    (2016.01)
   *A61B 90/30*    (2016.01)
   *G02B 21/04*    (2006.01)

(52) U.S. Cl.
   CPC ............ *G02B 21/02* (2013.01); *G02B 21/025* (2013.01); *G02B 21/04* (2013.01)

(56) References Cited

U.S. PATENT DOCUMENTS

| | | |
|---|---|---|
| 2010/0016662 A1 | 1/2010 | Salsman et al. |
| 2010/0125170 A1 | 5/2010 | Sugimoto |

FOREIGN PATENT DOCUMENTS

| | | |
|---|---|---|
| JP | 2002233494 A | 8/2002 |
| JP | 2010099178 A | 5/2010 |
| JP | 2015119827 A | 7/2015 |
| WO | 2005110186 A2 | 11/2005 |
| WO | 2007072556 A1 | 6/2007 |

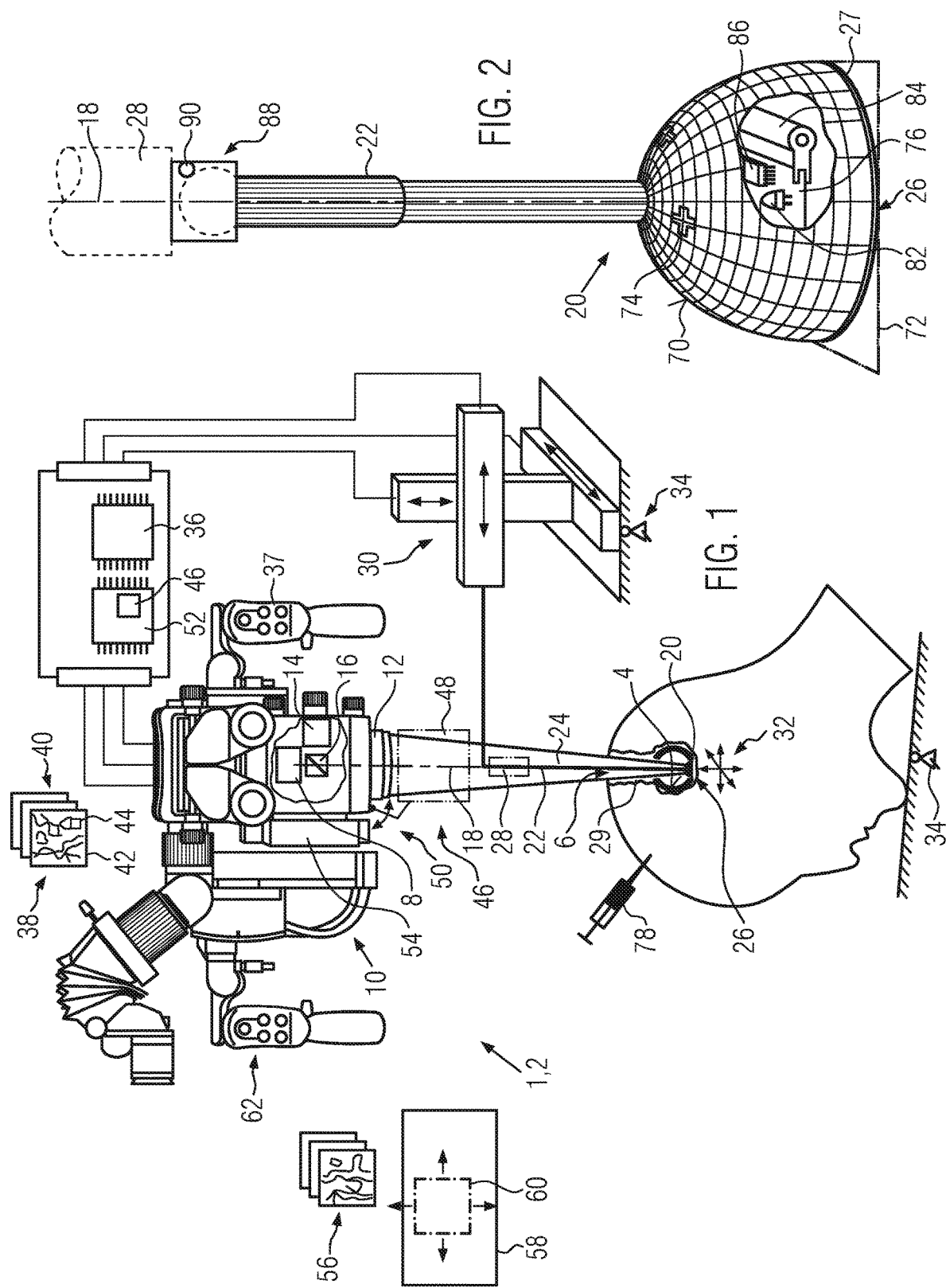

CATADIOPTRIC MEDICAL IMAGING SYSTEM FOR OBSERVING THE INSIDE WALL OF A SURGICAL CAVITY

CROSS REFERENCE TO RELATED APPLICATIONS

This application claims priority of European patent application number 18160210.3 filed Mar. 6, 2018, the entire disclosure of which is incorporated by reference herein.

FIELD OF THE INVENTION

The invention relates to a catadioptric medical imaging system for observing the inside wall of a surgical cavity.

BACKGROUND OF THE INVENTION

During surgery, it is often difficult for the surgeon to gain information about the structure of a surgical cavity, in particular if the surgical cavity widens and forms an undercut, which cannot be observed in a front view.

SUMMARY OF THE INVENTION

The object of the present invention is to provide a system and a method for obtaining such information.

This object is achieved according to the invention in that the catadioptric medical imaging system for observing the inside wall of a surgical cavity comprises a camera device and a convex catoptric mirror adapted to be inserted into the surgical cavity.

The invention also relates to a method for imaging an inside wall of a surgical cavity, the method comprising the steps of inserting a convex catoptric mirror into the surgical cavity and directing the field of view of a camera device manually or automatically onto the catoptric mirror.

Finally, the invention also relates to the use of a convex catoptric mirror with a camera device directed onto the catoptric mirror for imaging an inside wall of a surgical cavity.

Using the convex catoptric mirror allows the surgeon to gain an overview of the interior of the surgical cavity as the inside wall of the surgical cavity is reflected in the catoptric mirror. The convex shape allows the field of view to be expanded across a large part of the surgical cavity. The arm allows the convex catoptric mirror to be placed within the cavity. The camera device records the mirror image of the inside wall of the surgical cavity.

The catadioptric medical imaging system may in particular be a surgical microscope, such as a microscope for brain surgery.

The invention may be further improved by adding one or more of the following features, which may be combined independently of one another as each of the following features is advantageous on its own. The following additional features apply to both the method and the system according to the invention.

For example, the catoptric mirror may be located within the surgical cavity and within a field of view of the camera device during surgery. The catoptric mirror may be a separate part which may be deposited in the surgical cavity, e.g. by having a releasable coupling that may be attached to an arm. As such a coupling, the arm may be provided with a suction cap which is adapted to engage a surface, e.g. the mirror surface for depositing it in or removing it from the surgical cavity. Alternatively, the catoptric mirror may be attached permanently to an arm. The coupling is preferably provided with a remote release so that the mirror can be detached from the arm when already located within the cavity.

The catoptric mirror may be arranged in a fixed position relative to the optical axis of the camera device. In particular, the catoptric mirror may be centered about the optical axis of the camera device. The fixed position of the catoptric mirror relative to the optical axis facilitates any correction of distortion in the mirror image which is due to the convex shape of the mirror.

In another advantageous embodiment, the catoptric mirror may be a fish-eye mirror. In particular, the diagonal angle of view in an image recorded by the camera device of the catoptric mirror may be at least 120°, preferably at least 180°. In another embodiment, the angle of view in the image of the catoptric mirror recorded by the camera device may be at least 120°, preferably at least 180° in at least one of the horizontal and vertical image direction.

The typical size of a diameter of the catoptric mirror may between 5 mm and 20 mm.

The base of the mirror may be circular or polygonal. In particular, the base of the mirror may correspond to the shape of the field of view of the camera device. Any convex shape, such as e.g. hemispherical, elliptoid, paraboloid or hyperboloid, is possible. The shape of the base may be adapted to the shape and/or size of the surgical cavity. A set of catoptric mirrors having different sizes and/or shapes may be provided. For quick replacement, the catoptric mirrors may be mounted on the arm by a quick-release holder.

The catoptric mirror may be provided with at least one marker which reflects or emits light in a manner which differs from the immediate surroundings of the marker. For example, the marker may have a reflectance outside the visible light spectrum in at least some wavelengths, which is higher or lower than the reflectance of the immediate surroundings of the marker in these wavelengths. The reflectance of the marker may be restricted to at least some wavelengths outside the visible spectrum such as at least one of UV, IR and NIR wavelengths. In the visible spectrum, reflectance of the marker may be the same as that of its immediate surroundings. Of course, the different reflectance of the marker may also comprise wavelengths in the visible-light spectrum.

In one embodiment, a light source may be comprised by the catoptric mirror, e.g. be arranged within the catoptric mirror. In such a case, transmissivity or transparency of the catoptric mirror may be different at the marker compared to the immediate surroundings of the marker. The light source may, preferably exclusively, emit light in at least some wavelengths of the UV, IR and/or NIR spectrum. The catoptric mirror may have transparency at least for light emanating from the inside of the catoptric mirror through the catoptric mirror.

The marker may, in another additional or alternative embodiment, be fluorescent.

The camera device may comprise a multispectral camera and/or a hyperspectral camera. The wavelengths in which fluorescence, reflectance or transmissivity of the marker differs from its immediate surroundings and in which the marker is thus visible, may be mapped to a separate spectral band of the multispectral or hyperspectral camera. Thus, one spectral range of the camera device may be used to register the catoptric mirror within the field of view while the remaining spectral bands are unaffected and may be used to image the surgical cavity.

Additionally or alternatively, the multispectral and/or hyperspectral camera may be used to obtain images of the surgical cavity using fluorescent light of at least one fluorophore. To trigger fluorescence of a fluorophore within the surgical cavity, the catoptric mirror may include a light source having a spectrum which includes wavelengths which trigger fluorescence in the at least one fluorophore.

The marker may be used to automatically detect the location and orientation of the catoptric mirror. The marker may also be used for focusing the camera device onto the catoptric mirror.

In another embodiment, the camera device may be provided with a controller, the controller being adapted to automatically adjust at least one of a field of view, a focal length and a distance setting of the camera device. In particular, the controller may be adapted to automatically adjust at least one of the field of view, the focal length and the distance setting of the camera device based on an image of the marker of the catoptric mirror, wherein the image is acquired by the camera device. In particular, the controller may be adapted to automatically fill the field of view with at least part of the catoptric mirror. These measures individually facilitate automatic operation of the catadioptric medical imaging system, as the controller may automatically detect the presence of the catoptric mirror and perform necessary adjustments of the camera device to obtain optimal resolution for the images of the interior of the surgical cavity. Thus, the information about the surgical cavity may be automatically obtained when the catoptric mirror is inserted into the surgical cavity. The controller may be a hardware device, such as an ASIC; it may be implemented in software; or it may be implemented using a combination of hardware and software.

The catoptric mirror may be hand-held. In this case, the arm may comprise a handle. Thus, the catoptric mirror may be manipulated by hand.

In another embodiment, the arm is at least indirectly attached to the camera device, e.g. by being attached to a frame of the catadioptric medical imaging system. The arm may be telescopic, so that its length may be adjusted to the depth of the surgical cavity. In particular, the arm may comprise a handle for manual handling and may in addition be mounted to the frame.

The arm may be a highly flexible tube, such as for an endoscope, and be adapted to be rigidized on demand.

The catoptric mirror may be attached to the tissue during surgery without being connected to the arm. Towards this end, the base of the mirror may be provided with an attachment section, which may comprise an arrangement for establishing at least one of a chemical and mechanical bond with the tissue, such as a glue and/or spikes. Such a mirror may be lightweight e.g. by being hollow or filled with foam and having a foil as a mirror surface.

A drive system may be included to move the catoptric mirror relative to the camera device. Such a relative movability may be advantageous for surgical cavities which have a complex geometry and where small relative movements between the mirror and the camera device may be required to survey certain locations of the surgical cavity.

The drive system may be used to change the distance between the camera device and the catoptric mirror, e.g. by collapsing and extending the telescopic arm. Additionally or alternatively, the drive system may be adapted to move the catoptric mirror in a direction perpendicular to the optical axis of the camera device relative to the camera device.

The drive system is preferably adapted to be coupled to the controller. For example, the drive system of the catoptric mirror may provide positioning data which are representative of the position of the catoptric mirror relative to the camera device. The controller may be adapted to compute settings of the camera device, such as focal length and/or distance from the positioning data.

The arm may extend coaxial to the optical axis of the camera device. The arm may extend from a center point of the catoptric mirror. In such a configuration, the arm is placed at a location of the catoptric mirror which, in operation, would reflect the camera device and thus would not yield any information on the surgical cavity.

If a stereoscopic camera is used, the arm may be located coinciding with the bisector of the two optical axes of the two stereoscopic cameras.

In an advantageous embodiment, the arm is flexible in at least one of a direction perpendicular and parallel to the optical axis, to avoid damaging tissue in the surgical cavity. The flexibility may be obtained by at least one of manufacturing the arm at least sectionally from flexible material or providing at least one flexible joint at least one location along the arm.

A sensor may be provided, which is reactive to flexion of the arm and adapted to output a flexion signal representative of the amount of flexion of the arm. Such a sensor may be used to automatically stop any drive system which moves the catoptric mirror relative to the surgical cavity if a predetermined degree of flexion as represented in the flexion signal is reached. This is another measure for preventing damage to the tissue in the surgical cavity.

In another embodiment, the drive system may be adapted to preferably automatically move the catoptric mirror relative to the camera device such that the at least one marker is at a predetermined position within the field of view.

A focal length of the camera device may be adjusted such that the field of view of the camera device is filled by only part of the catoptric mirror. This allows a focus on specific parts of the surgical cavity or the catoptric mirror, respectively. In such a configuration, it may be particularly beneficial if the drive system is configured to move the catoptric mirror relative to the camera device and thus the field of view to different parts of the surgical cavity. Thus, the catadioptric medical imaging system may be adapted to scan the surface of the catoptric mirror and the mirror image of the surgical cavity.

The catadioptric medical imaging system may comprise an image processor which may be realized in hardware, software, or a combination of hardware and software. The image processor is preferably adapted to combine or stitch images of different parts of the catoptric mirror as recorded by the camera device to an output image, preferably a single output image. Combining more than one image to represent the mirror image on the catoptric as seen from the camera device increases resolution.

In another embodiment, the catadioptric medical imaging system may comprise an illumination device which is spaced apart from the catoptric mirror. In particular, the illumination device may be located outside the surgical cavity during surgery. The illumination device may be directed onto the catoptric mirror and thus may be used to illuminate the surgical cavity. Illumination may be carried out in the visible range and/or in at least one of the UV, IR and NIR range. The illumination device may also be used to trigger fluorescence of at least one fluorophore. Illumination by the illumination device may, for example, be performed by having the light from the illumination device be directed coaxial to the optical axis of the camera device.

In a further embodiment, a reflection of the illumination device of the catoptric mirror as recorded by the camera device may be used as a marker for positioning the catoptric mirror relative to the camera device as explained above.

If a convex catoptric mirror, such as a hemispherical mirror, is used, the images recorded by the camera device will be distorted. This may render visual inspection of the images by the surgeon difficult. Thus, it is advantageous if the catadioptric medical imaging system comprises a correction module adapted to correct distortion of the catoptric mirror. The correction module may comprise correction optics which are arranged between the catoptric mirror and the camera device. Such an optical correction device has the advantage that the full resolution of the camera may be used.

The correction module may also be implemented by hardware and/or software, and be part of an image processor of the imaging system.

Preferably, the output images from the image processor are corrected with respect to optical distortion by the convex catoptric mirror.

In the following, embodiments of the invention are described exemplarily with reference to the drawings. In the drawings, the same reference numerals are used for elements that correspond to each other with respect to function and/or design. According to the above description of possible additional features and their respective technical effects, a feature can be omitted from an embodiment if the technical effect associated with that feature is not beneficial for a particular application, and vice versa: an additional feature described above may be added to an embodiment if, for a particular application, the technical effect of that feature is advantageous.

BRIEF DESCRIPTION OF THE DRAWING VIEWS

In the drawings,

FIG. 1 shows a schematic representation of the catadioptric medical imaging system according to the invention, and FIG. 2 shows a schematic rendition of a catoptric mirror which is used in the catadioptric medical imaging system according to the invention.

DETAILED DESCRIPTION OF THE INVENTION

First, the design and function of a catadioptric medical imaging system 1, such as a surgical microscope 2 are explained with reference to FIG. 1. The catadioptric medical imaging system 1 is used for observing an inside wall 4 of a surgical cavity 6, such as a surgical cavity in brain surgery, but also for any other kind of surgical cavity.

The catadioptric medical imaging system 1 comprises a camera device 8 which may be located in an optics carrier 10 together with a lens 12, in particular a microscope lens. The catadioptric medical imaging system 1 may also comprise an illumination device 14 which may also be included in the optics carrier 10. A beam splitter 16 may be provided to add light from the illumination device 14 coaxial to an optical axis 18 of the camera device 8 and directed towards the surgical cavity 6. Light directed towards the camera device 8 from the surgical cavity 6 is separated from light from the illumination device 14 by the beam splitter 16.

The camera device 8 may comprise a multispectral camera or a hyperspectral camera. The camera device 8 may comprise more than one single camera, e.g. for stereoscopic imaging. The camera device 8 may be sensitive in at least one of the UV, IR and NIR spectrum. Additionally or alternatively, the camera device 8 may comprise a stereoscopic camera, so that three-dimensional images of the interior of the surgical cavity 6 may be acquired.

The illumination device 14 may provide illumination light in at least one of the visible light spectrum, the UV spectrum, the IR spectrum and the NIR spectrum.

In order to view the inside wall 4 of the surgical cavity 6, a convex catoptric mirror 20 is provided. The catoptric mirror 20 is adapted to be inserted into the surgical cavity 6. For insertion, an arm 22 is provided.

The convex catoptric mirror 20 is arranged in the field of view 24 of the camera device 8, preferably such that the field of view 24 is filled at least almost completely by the catoptric mirror 20.

The catoptric mirror 20 is preferably a fish-eye mirror, which has a diagonal angle of view of at least 120°, preferably of 180°. Even more preferably, the angle of view in at least one of the horizontal and vertical direction of an image recorded by the camera device 8 is at least 120°, preferably 180°. This allows most or all of the surgical cavity 6 to be surveyed if the convex catoptric mirror 20 is at or close to the inside wall 4 in the surgical cavity 6 opposite the camera device 8. The shape of the convex catoptric mirror 20 may, for example, be (hemi-) spherical, parabolic, hyperbolic or ellipsoid. The convex catoptric mirror 20 may have rotational symmetry and may be aligned with the optical axis 18 of the camera device 8, its base 26 which faces away from the camera device 8 being perpendicular to the optical axis 18.

The arm 22 may be configured for manual handling by the surgeon or an assistant by having a handle 28. In order to avoid damage to any tissue 29 in the surgical cavity 6, the arm 22 is flexible in at least one of its longitudinal direction and a direction perpendicular thereto, preferably both. The stiffness of the arm 22 is preferably not higher than the stiffness of the tissue 29 within the surgical cavity 6. A remotely releasable coupling may be provided for releasably attaching the catoptric mirror to the arm.

In another embodiment, the catoptric mirror is deposited by itself in surgical cavity. The base 26 may be provided with an attachment section 27 for attaching it to the tissue 29. This is particularly useful when the catoptric mirror 20 stays with the surgical cavity 6 without an arm 22. The attachment section 27 may comprise a means for establishing at least one of a chemical and a mechanical connection with the tissue 29, e.g. a glue and/or spikes or hooks.

Preferably, however, the catoptric mirror 20 is and/or may be adapted to be releasably attached to a drive system 30. The drive system 30 is adapted to move the catoptric mirror 20 relative to the camera device 8, preferably in all three spatial dimensions, as indicated by arrows 32. The drive system 30 may be fixed relative to a support frame 34 of the catadioptric medical imaging system 1, which support frame is only indicated schematically. The support frame 34 is preferably stationary with respect to the surgical cavity 6. The optics carrier 10 may be movable with respect to the support frame 34, e.g. by being attached to a pivotable cantilevered boom which supports the optics carrier 10.

The catadioptric medical imaging system 1 may be provided with a controller 36 for controlling the drive system 30, e.g. in response to manipulators 37 of the catadioptric medical imaging system 1, which manipulators 37 are operated by the surgeon. This enables the catoptric mirror 20 to be moved within the surgical cavity 6 and thus allows surgical cavities with complex interior shapes, such as undercuts, to be surveyed.

In operation, the camera device 8 will output image data 38, e.g. as a time series 40 of frames 42, each frame 42 consisting of a plurality of pixels 44.

Due to the shape of the convex catoptric mirror 20, the images gathered from the catoptric mirror 20 as represented by or in the frames 42 will be distorted. This distortion may impede visual analysis of the frames 42 by a surgeon or assistant.

To correct or at least reduce distortion caused by the catoptric mirror 20, a correction module 46 may be provided. The correction module 46 may comprise correction optics 48 which are preferably arranged between the surgical cavity 6 and the camera device 8. Preferably, the correction optics 48 can be quickly mounted and unmounted, e.g. be moved into the field of view 24 of the camera device 8. For example, a support 50 for pivoting the correction optics 48 in front of the camera device 8, in particular the lens 12, and back may be provided.

The catadioptric medical imaging system 1 may further comprise an image processor 52, which may also comprise the correction module 46 or a part thereof, which in this case may be implemented as software or electronic hardware. The correction module 46 of the image processor 52 is adapted to correct distortion of the convex catoptric mirror 20 in the image data 38. For example, the image processor 52 may be adapted to compute distortion-free three-dimensional images from stereoscopic images of the catoptric mirror 20. The image distortion correction performed by the image processor 52 may be used together with the correction optics 48 to obtain optimum results.

The catadioptric medical imaging system 1 may further comprise at least one display 54, which may be integrated into the optics carrier 10. The display 54 is coupled to the image processor 52 and adapted to display output image data 56 which have been derived from the image data 38. For example, the output image data 56 may comprise an output frame 58 based on at least one distortion-corrected frame 42. The display 54 may only show a part 60 of the output frame 58. The part 60 may be moved in the output frame 58 depending on the operation of manipulators 62 of the catadioptric medical imaging system 1.

Movement of the part 60 within the output frame 58 may also be effected by including a virtual reality system in the catadioptric medical imaging system 1, such as movement-sensitive goggles as a display 54.

FIG. 2 shows an exemplary embodiment of the convex catoptric mirror 20 and the arm 22. The convex catoptric mirror 20 is shown only for explanatory purposes as having a hemispherical mirror surface 70. Any other shape which allows the interior of the surgical cavity to be surveyed may be used. The base 26 of the catoptric mirror 20 is shown to be circular, but can also be of any shape, e.g. polygonal, such as rectangular, as indicated by phantom lines 72. The rectangular base 72 may be adapted to correspond, in its proportions, to the side ratio of a frame 42 as recorded by the camera device 8. A rectangular base 72 allows the field of view 24 to be completely filled by the catoptric mirror 20.

The catoptric mirror 20 may be provided with at least one marker 74 having a fluorescence, reflectance and/or transmissivity which differs from its immediate surroundings. For example, the marker 74 may have an increased or reduced reflectance in a non-visible part of the light spectrum, such as UV, IR or NIR, or in one or more wavelengths of the visible-light spectrum. The marker 74 may, additionally or alternatively, be fluorescent. The marker 74 may be used to adjust the position of the catoptric mirror 20 relative to the optical axis 18 of the camera device 8, either manually or using the drive system 30. A plurality of markers 74 can be arranged around the optical axis 18. The marker 74 may also be or include a light source, such as an LED.

In another embodiment, the catoptric mirror 20 may be at least sectionally transparent or semi-transparent to allow light to pass from the interior of the catoptric mirror 20 to the outside. In particular, transparency at a marker 74 may be different to transparency of the immediate surrounding of the marker 74. Thus, the light passing through the markers 74 allows said markers 74 to be recognized and identified automatically.

A light source 76 may be arranged inside the catoptric mirror 20. The light source 76 may emit illumination light in at least one of the visible light spectrum, the UV spectrum, the IR spectrum and the NIR spectrum. The light from the light source 76 may be used to trigger fluorescence in the inside walls 4 of the surgical cavity 6 if at least one fluorophore 78 (FIG. 1) is injected into the tissue 29 bordering the surgical cavity 6. The catadioptric medical imaging system 1 may be provided with a band-stop filter (not shown) for blocking light from the light source 76.

The light source 76 may e.g. comprise at least one (or more) LED(s) 82. The catoptric mirror 20 may include a power source 84 for driving the light source 76 and e.g. a communication module 86 for wired or wireless connection to e.g. the controller 36 of the catadioptric medical imaging system 1. The light source 76 may also be powered through a power line which extends through the arm 22.

The arm 22 may be telescopic, as exemplarily shown in FIG. 2. The extension or collapse of the arm 22 may be driven by the drive system 30.

The arm 22 may be provided at its end with a coupling 87 for releasably engaging with the catoptric mirror 20 e.g. by being provided at its end with a suction cap for engaging the mirror surface 70 using a vacuum. The coupling 87 may be used for depositing and picking up the catoptric mirror 20.

Instead of or additionally to forming the arm 22 from flexible material, one or more joints 88 may be provided between the catoptric mirror 20 and the handle 28 (if present) or the drive system 30. The joint 88 is preferably adapted to provide flexibility to the arm 22. Again, the flexibility of the arm should be higher than the compressibility of the tissue 29 to prevent tissue damage. The joint 88 is preferably flexible and thus may exert a restoring force if deflected.

A flexion sensor 90 may be provided, which is preferably connected to the controller 36. The flexion sensor 90 is adapted to output a flexion signal which is representative of an amount of flexion in the joint 88 or of the arm 22 as a whole. The controller 36 may be adapted to stop or revert any motion of the drive system 30 if the flexion as represented by the flexion signal exceeds a predetermined amount. Additionally or alternatively, an alarm signal may be triggered by the flexion signal if the amount of flexion of the arm 22 is too high. For example, the arm 22 may be provided with a buzzer and/or an LED (not shown) for outputting the alarm signal depending on the flexion signal.

If the mirror 20 is to be attached to the tissue 29, it should be light weight. In such a configuration, the catoptric mirror 22 may be hollow or filled with a lightweight material such as foam. The mirror surface 70 may be formed by a foil.

REFERENCE NUMERALS 1 catadioptric medical imaging system
2 surgical microscope
4 inside wall of surgical cavity 6 surgical cavity
8 camera device
10 optics carrier
12 lens, in particular microscope lens
14 illumination device
16 beam splitter
18 optical axis
20 convex catoptric mirror
22 arm
24 field of view of camera device
26 base of convex catoptric mirror
27 attachment section
28 handle
29 tissue of the surgical cavity
30 drive system
32 arrows
34 support frame of catadioptric medical imaging system or microscope
36 controller
37 manipulator
38 image data
40 times series
42 frame
44 pixel
46 correction module
48 correction optics
50 support for correction optics
52 image processor
54 display
56 output image data
58 output frame
60 displayed part of output frame
62 manipulator
70 mirror surface
72 phantom line
74 marker
76 light source
78 fluorophore
82 LED
84 power source
86 communication module
87 coupling
88 joint
90 flexion sensor

What is claimed is:

1. A catadioptric medical imaging system (1) for observing an inside wall (4) of a surgical cavity (6), the catadioptric medical imaging system (1) comprising:
    a camera device (8);
    a convex catoptric mirror (20) spaced from the camera device (8), wherein the catoptric mirror (20) is adapted to be inserted into the surgical cavity (6);
    a correction module (46) adapted to correct distortion of the catoptric mirror (20); and
    an image processor (52), wherein the correction module (46) is a part of the image processor (52).

2. The catadioptric medical imaging system (1) according to claim 1, wherein the catoptric mirror (20) is a fish-eye mirror.

3. The catadioptric medical imaging system (1) according to claim 1, wherein the catoptric mirror (20) includes a marker (74) which differs from immediate surroundings of the marker (74) in at least one of reflectance, fluorescence, and transparency.

4. The catadioptric medical imaging system (1) according to claim 3, wherein the marker (74) reflects and/or emits light outside the visible light spectrum.

5. The catadioptric medical imaging system (1) according to claim 4, further comprising a controller (36) adapted to automatically adjust a field of view (24) of the camera device (8) to the catoptric mirror (20) based on the marker (74).

6. The catadioptric medical imaging system (1) according to claim 1, further comprising a light source (76) carried by the catoptric mirror (20).

7. The catadioptric medical imaging system (1) according to claim 1, further comprising a controller (36) adapted to automatically adjust a field of view (24) of the camera device (8) to the catoptric mirror (20).

8. The catadioptric medical imaging system (1) according to claim 7, wherein the controller (36) is adapted to automatically fill the field of view (24) of the camera device (8) with the catoptric mirror (20).

9. The catadioptric medical imaging system (1) according to claim 1, further comprising an arm (22), wherein the catoptric mirror (20) is mounted to the arm (22).

10. The catadioptric medical imaging system (1) according to claim 1, further comprising a drive system (30) adapted to move the catoptric mirror (20) relative to the camera device (8).

11. The catadioptric medical imaging system (1) according to claim 1, wherein the medical imaging system (1) is a surgical microscope (2).

12. A catadioptric medical imaging system (1) for observing an inside wall (4) of a surgical cavity (6), the catadioptric medical imaging system (1) comprising:
    a camera device (8);
    a convex catoptric mirror (20) spaced from the camera device (8), wherein the catoptric mirror (20) is adapted to be inserted into the surgical cavity (6); and
    a correction module (46) adapted to correct distortion of the catoptric mirror (20), wherein the correction module (46) comprises correction optics (48) arranged between the camera device (8) and the catoptric mirror (20).

13. A method of imaging an inside wall (4) of a surgical cavity (6), comprising the steps of:
    inserting a convex catoptric mirror (20) into the surgical cavity (6);
    arranging the catoptric mirror (20) in a field of view (24) of a camera device (8); and
    correcting distortion of the catoptric mirror (20) in a correction module (46), wherein the correction module (46) is a part of an image processor (52).

* * * * *